United States Patent
Limer et al.

(10) Patent No.: US 7,599,516 B2
(45) Date of Patent: Oct. 6, 2009

(54) MACHINE VISION COUNTING SYSTEM APPARATUS AND METHOD

(75) Inventors: Daniel J. Limer, Royal Oak, MI (US); David A. Lang, Commerce Township, MI (US); Christopher S. Burt, Plymouth, MI (US); Philip R. Gouin, Cumberland, RI (US); Nelson D. Tarr, Ashland, MA (US); Randall D. Dischinger, Madison Heights, MI (US)

(73) Assignee: Illinois Tool Works Inc., Glenview, IL (US)

( * ) Notice: Subject to any disclaimer, the term of this patent is extended or adjusted under 35 U.S.C. 154(b) by 784 days.

(21) Appl. No.: 11/331,343

(22) Filed: Jan. 13, 2006

(65) Prior Publication Data

US 2007/0047980 A1 Mar. 1, 2007

Related U.S. Application Data

(60) Provisional application No. 60/710,188, filed on Aug. 23, 2005.

(51) Int. Cl.
*G06K 9/00* (2006.01)

(52) U.S. Cl. .................. 382/100; 211/88.01; 453/4; 453/7

(58) Field of Classification Search .................. None
See application file for complete search history.

(56) References Cited

U.S. PATENT DOCUMENTS

| | | | |
|---|---|---|---|
| 4,446,481 A * | 5/1984 | Edamatsu et al. | 348/132 |
| 4,597,091 A | 6/1986 | Blake | |
| 5,422,831 A * | 6/1995 | Misra et al. | 702/81 |
| 5,440,648 A | 8/1995 | Roberts et al. | |
| 5,558,231 A | 9/1996 | Weier | |
| 5,671,262 A | 9/1997 | Boyer et al. | |

(Continued)

FOREIGN PATENT DOCUMENTS

EP 0371881 A2 6/1990

(Continued)

OTHER PUBLICATIONS

International Search Report mailed Mar. 25, 2008; 2 pages.

*Primary Examiner*—Brian P Werner
*Assistant Examiner*—Jayesh Patel
(74) *Attorney, Agent, or Firm*—Mark W. Croll; Lisa Guilt; Levenfeld Pearlstein, LLC

(57) ABSTRACT

A machine-vision-based counter includes an image acquisition component (imager), wherein light provides discrimination between a background field and imageable units located away from the imager. The imager outputs data representing the field and units; an image processor receiving imager data finds countable units therein. An operator interface accepts command inputs and presents count output. A controller manages image acquisition, processor, and operator interface functions. A counting method includes configuring an imager to detect light, directing light from a source to units positioned to be detected by the imager, and directing the light to the imager. The method includes discriminating between a background field and imageable units; providing, as an imager output, data representing the field and units; configuring an image-processor to receive imager data; configuring the processor to interpret the data as counted units on a background field; and configuring an operator interface to present a count result.

11 Claims, 11 Drawing Sheets

U.S. PATENT DOCUMENTS

| | | |
|---|---|---|
| 5,768,327 A | 6/1998 | Pinto et al. |
| 5,903,347 A | 5/1999 | Girvin et al. |
| 5,907,493 A * | 5/1999 | Boyer et al. ................ 700/231 |
| 6,167,150 A * | 12/2000 | Michael et al. ............. 382/149 |
| 6,266,437 B1 * | 7/2001 | Eichel et al. ................ 382/149 |
| 6,363,687 B1 | 4/2002 | Luciano et al. |
| 6,370,215 B1 | 4/2002 | Pinto et al. |
| 6,445,817 B1 | 9/2002 | de la Torre-Bueno |
| 6,483,935 B1 * | 11/2002 | Rostami et al. ............. 382/141 |
| 6,497,339 B1 | 12/2002 | Geltser et al. |
| 6,554,157 B2 | 4/2003 | Geltser et al. |
| 6,574,580 B2 * | 6/2003 | Hamilton .................... 702/128 |
| 6,610,973 B1 * | 8/2003 | Davis, III ................. 250/222.1 |
| 6,738,723 B2 | 5/2004 | Hamilton |
| 6,944,323 B1 * | 9/2005 | Parani et al. ................ 382/141 |
| 6,944,324 B2 | 9/2005 | Tran et al. |
| 6,997,341 B2 | 2/2006 | Pearson et al. |
| 7,006,214 B2 | 2/2006 | Rzasa et al. |
| 7,006,886 B1 * | 2/2006 | Huet et al. .................. 700/110 |
| 7,115,857 B1 * | 10/2006 | Berke ....................... 250/222.1 |
| 2002/0033884 A1 | 3/2002 | Schurr |
| 2003/0204357 A1 * | 10/2003 | Hamilton .................... 702/128 |
| 2005/0111724 A1 | 5/2005 | Macy et al. |
| 2005/0286753 A1 | 12/2005 | Ho |
| 2005/0288906 A1 | 12/2005 | Drennen, III et al. |
| 2006/0025884 A1 | 2/2006 | Henkel |
| 2006/0045323 A1 * | 3/2006 | Ateya ........................ 382/141 |
| 2006/0058725 A1 | 3/2006 | Handfield et al. |
| 2006/0098193 A1 | 5/2006 | Rzasa et al. |

FOREIGN PATENT DOCUMENTS

| | | |
|---|---|---|
| JP | 09-062824 | 3/1997 |
| JP | 09-124142 | 5/1997 |
| JP | 09-231342 | 9/1997 |

* cited by examiner

MACHINE VISION COUNTING SYSTEM APPARATUS AND METHOD

CROSS-REFERENCE TO RELATED APPLICATIONS

This application claims priority to provisional U.S. patent application entitled MACHINE VISION COUNTING SYSTEM APPARATUS AND METHOD, filed Aug. 23, 2005, having application No. 60/710,188, the disclosure of which is hereby incorporated by reference in its entirety.

FIELD OF THE INVENTION

The present invention relates generally to a counting system. More particularly, the present invention relates to optically based unit counting machines.

BACKGROUND OF THE INVENTION

There are approximately 120,000 pharmacies in the United States alone, with a current growth rate on the order of 10% per year. In some high volume pharmacies, robots are used to fill prescriptions. In some medium and low volume pharmacies, prescriptions are counted by other methods, such as manually, using weighing or counting scales, or using semi-automated apparatus such as optical beam pour through systems.

In manual counting, a pharmacist or assistant (a dispensing agent) reviews a prescription, finds the corresponding stock bottle, pours a number of units from the stock bottle, typically onto a specially-configured tray, then counts out the prescribed number of units, decanting these into a receiver bottle and returning any remaining units to the stock bottle. The receiver bottle is labeled with appropriate information, such as the prescriber's name, the name and dosage of the prescription, usage instructions, dates, and the like. This procedure is comparatively slow, and can be cumbersome.

Weighing or counting scales can quicken dispensing while providing an accurate count. With some counting scales, a first unit or known plurality of units is placed on the scale and identified as a reference weight. Next, a generally unknown number of units are placed on the scale, and the scale computes a number of units on the scale based on the reference weight. Units may be added to and removed from the scale until the desired number is indicated by the scale. It will be understood that the same operation may be performed manually, using weight readings and calculating the desired result. While generally accurate and faster than manual processes under some circumstances, a counting scale has no inherent provision for identifying damaged units, and will typically provide an integer result by including some roundoff in the computation to adjust for slight measurement discrepancies. Such devices can have reduced performance due to sample-to-sample or batch-to-batch piece weight variations, which can cause absolute count errors.

Other counting systems, such as optical beam pour through systems, also referred to as tablet counters, employ troughs and flow regulation to direct units past an optical detector, which counts the units as they slide past. Such devices may be insensitive to such errors as sample-to-sample or batch-to-batch weight variations, and may detect some types of unit defects, ignore small fragments, or otherwise include features or properties other than fundamental unit counting. Typical pour through devices rely on manual interaction by the agent during the pour through process, and may require rerunning a count—that is, transferring the units from the destination container to an intermediate container and pouring them back through—if more than the prescribed number of units are poured through initially.

Tradeoffs in using known weight-based and optical systems can include control of contamination, management of detected unit defects such as fragments of various sizes, and calibration requirements. While weight-based systems require periodic calibration to ensure accuracy, optical systems are substantially insensitive to drift characteristic of weight transducers. This may be offset by size and cost considerations, wherein pour through optical systems demand comparatively heavy use to justify resource commitment involved.

Accordingly, there is a need in the art for a counting system for pharmacy and other applications that integrates in a self-contained apparatus a machine-vision-based unit detector with associated control and message management functions.

SUMMARY OF THE INVENTION

The foregoing needs are met, to a great extent, by the present invention, wherein an apparatus is provided that in some embodiments provides a self-contained unit counter with an illuminated stage, a camera, an image analyzer, a touch-screen display/operator interface, and a communication link to an external environment.

In accordance with one embodiment of the present invention, a machine-vision-based counter for counting discrete units is presented. The counter includes an image acquisition component configured to detect light having at least one wavelength, wherein the light provides discrimination between a background field and a quantity of imageable units located at a distance from the image acquisition component, and to provide, as an output, data representing the field and the units, an image processor configured to receive data from the image acquisition component, and further configured to interpret the data as a field image whereon are superimposed a quantity of countable units, an operator interface component configured to present a count result output from the counter and to accept at least one command input to the counter, and a counter controller configured to manage at least the image acquisition component, image processor, and operator interface component functions of the counter.

In accordance with another embodiment of the present invention, a machine-vision-based counting method is presented. The counting method includes configuring an image acquisition component to detect light having at least one wavelength, directing light from a light source to units positioned to be detected by the image acquisition component, thereafter directing the light at least in part to the image acquisition component, discriminating between a background field and a quantity of imageable units located thereon, providing, as an image acquisition component output, data representing the field and the units, configuring an image processor to receive the data from the image acquisition component, configuring the image processor to interpret the received data as a background field whereon are superimposed a counted quantity of imageable units, and configuring an operator interface component to present a count result from the image processor.

In accordance with yet another embodiment of the present invention, a machine-vision-based counting system is presented. The counting system includes a counter system control function, a stage illumination function whereby the units to be counted by the system are lighted, a stage image acquisition function under the direction of the control function, using the illumination function lighting to acquire an image, a counter system unit geometry access function, wherein unit shape information is provided in a form usable within the counter, a unit discrimination function, whereby an individual unit within the image is identified in accordance with unit shape information, a unit count function, wherein an individual unit within the image is counted and the image managed to allow further discrimination and count operations, a unit count reporting function, wherein a numerical value for unit count is generated by the counter, a barcode scanner configured to detect data encoded according to at least one specified barcode system, and a counter system control function security subfunction, wherein the security subfunction includes a security information access function and a security status report task, wherein at least one security good indication is provided under conditions of all affirmative procedures completed successfully and no negative events invoked.

There have thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments, and of being practiced and carried out in various ways. It is also to be understood that the phraseology and terminology employed herein, as well as the abstract, are for the purpose of description, and should not be regarded as limiting.

As such, those skilled in the art will appreciate that the conception upon which this disclosure is based may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

DETAILED DESCRIPTION OF PREFERRED EMBODIMENTS OF THE INVENTION

Figure 1:
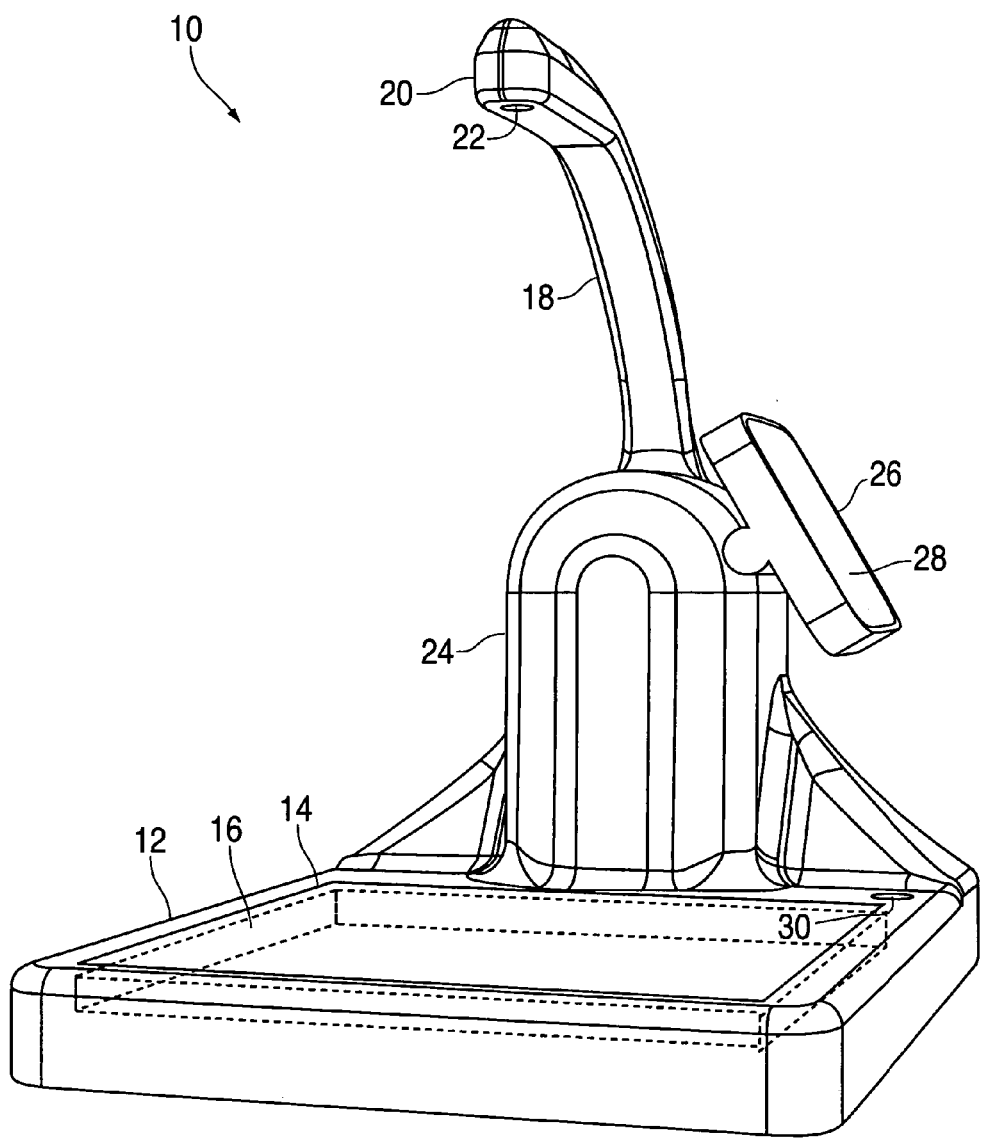
FIG. 1 is a perspective view of a counter according to one embodiment of the invention.

The invention will now be described with reference to the drawing figures, in which like reference numerals refer to like parts throughout. The present invention provides an apparatus and method that in some embodiments provides a counter that uses machine vision for pharmacy dispensing and like applications.

FIG. 1 shows a first embodiment of a counter 10, having a base 12 for placement of the counter 10 on a surface. The counter 10 includes a stage 14 for positioning of units to be counted, an illuminator 16 oriented to provide illumination upward from the upper surface of the stage 14, and a neck 18, extending upward from the vicinity of the stage 14, that positions an imager head 20. The imager head 20 affixes and directs an image acquisition component (imager) 22 toward the stage 14, permitting the imager 22 to acquire an image of any materials placed on the stage 14 and backlit by the illuminator 16. A circuit housing 24, configured to enclose electronic circuitry for operation of the counter 10, is, in the embodiment shown, at least partially integrated into the structure of the counter 10. An operator interface cluster 26, configured to provide display and input for a user, is likewise integrated at least in part into the structure of the counter 10. The operator interface cluster 26 includes a display 28 that may be tiltable, and that may include touch screen function in some embodiments. A power control in the form of a low-profile pushbutton switch 30 is positioned on the surface of the base 12. The counter 10 of FIG. 1 is in the form of a single, unitized apparatus including the base 12, the stage 14 and illuminator 16, the imager head 20, a processor contained within a circuit housing 24, and an operator interface 26.

Figure 2:
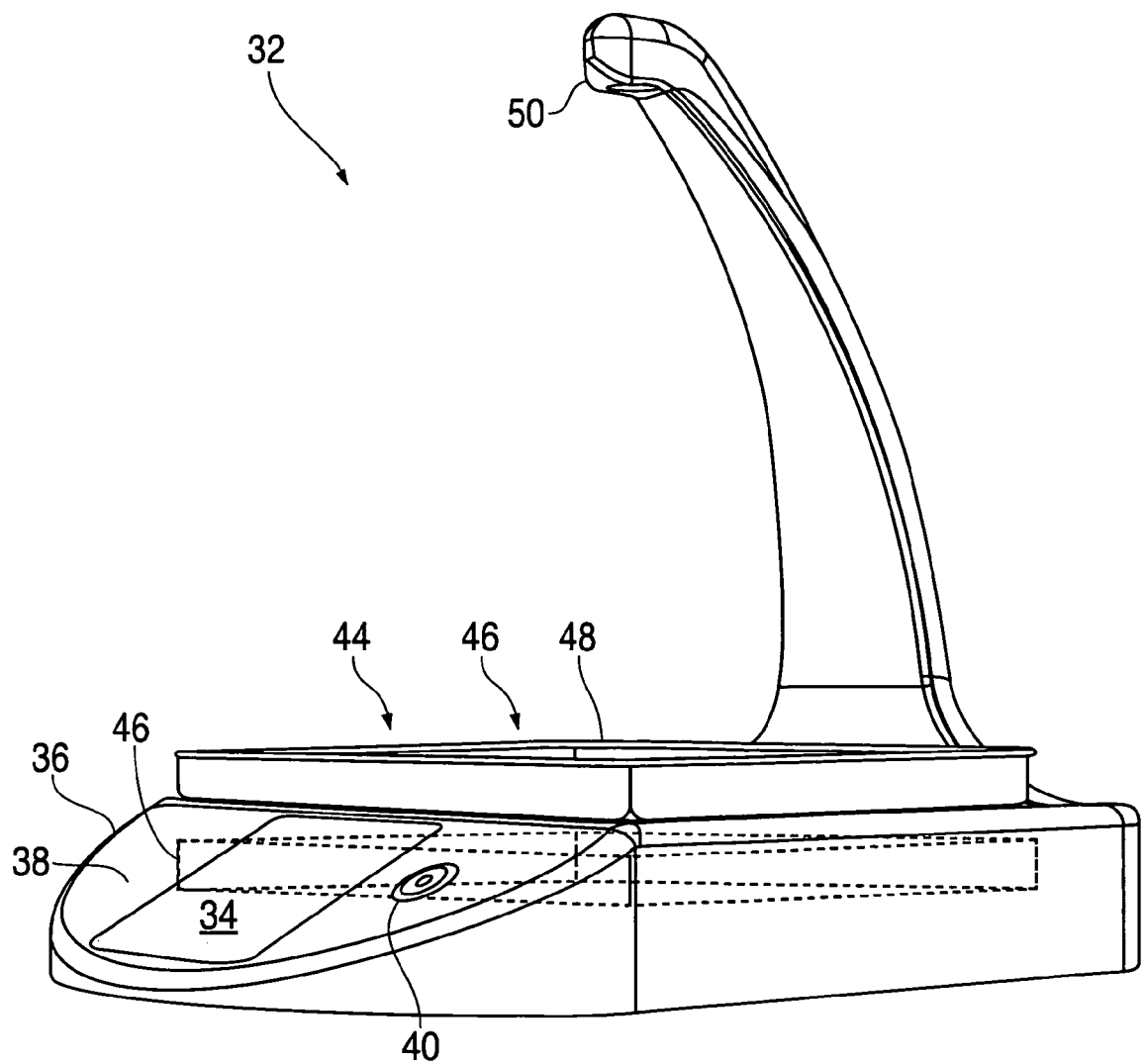
FIG. 2 is a perspective view of a counter according to another embodiment of the invention.

FIG. 2 shows a second embodiment of a counter 32. This embodiment differs from the embodiment of FIG. 1 in having an operator interface cluster 34 integrated into a base 36 on a sloped face 38 thereof, while a power switch 40 is located adjacent to the operator interface cluster 34. Electronic components for controlling the counter 32 are located within the base 36, beneath a stage 44 and an illuminator 46, rather than in a housing 24 integrated in part into the neck 18 as shown in FIG. 1. Shown in this embodiment is a user-supplied and user-removable tray 48, which tray 48 may be washable, sterilizable, and/or disposable, and which is substantially transparent over at least a floor area thereof—that is, a bottom surface surrounded at least in part by walls—to such portion of the electromagnetic spectrum as is used for illumination. Such a tray 48 may be smaller in extent than the illuminator 46 in at least some embodiments, which may tend to prevent units from resting thereon without being detectable. The tray 48 may be self-aligning in some embodiments, such as by fitting into a similarly-sized recess in the surface of the stage 44, by having alignment fittings in the tray 48 and stage 44 that establish a preferential position for the tray 48 on the stage 44, or by having another alignment provision. A tray 48 similar to that shown in FIG. 2 may be suitable for use with embodiments such as those of FIG. 1, above, and FIG. 3, below, as well. The counter 32, like the counter 10 of FIG. 1, is in the form of a single, unitized apparatus including, in this embodiment, an imager head 50, the stage 44 enclosing the illuminator 46, a controller contained within the base 36, and the operator interface 34. The stage 44, illuminated from below by the illuminator 46, constitutes a background field for units placed on the stage 44, allowing the imager head 50 to be limited in its field of view to the area so illuminated.

Figure 3:
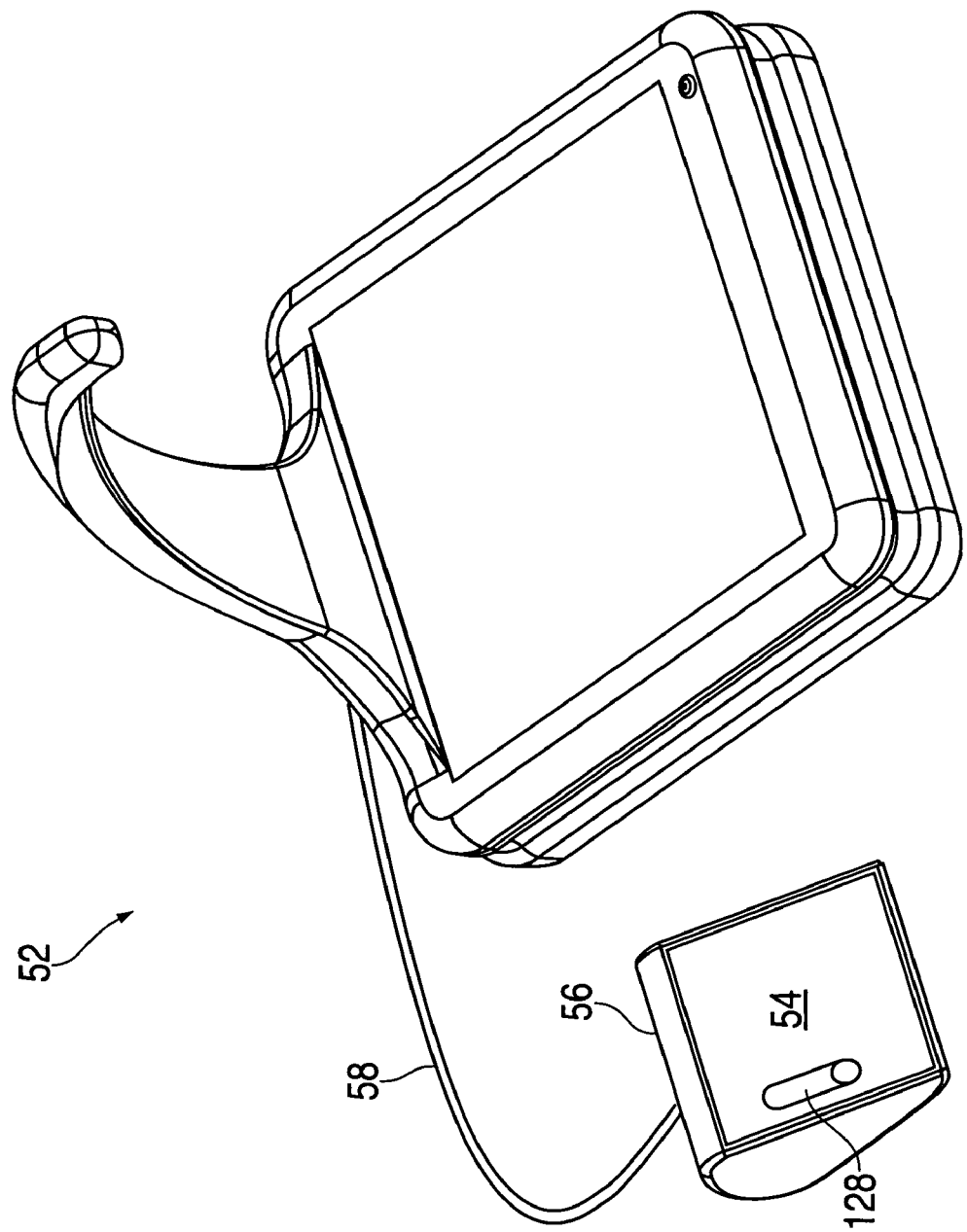
FIG. 3 is a perspective view of a counter according to another embodiment of the invention.

FIG. 3 shows a counter 52, substantially similar to the counters 10 of FIG. 1 and 32 of FIG. 2, wherein an operator interface 54 is located on a pendant 56 connected to the counter 52 by a cable 58. This arrangement, or a similar one wherein the pendant 56 is connected using a wireless link and may be separately powered, may be used in lieu of a more fully integrated apparatus in some applications. An orientation sensor 128 or selector may be provided, and may have the form, for example, of a tilt switch or absolute accelerometer embedded within the pendant 56, or may consist of a setup option for the processor. A display orientation provision based on such a selector or sensor may be used in some embodiments to rotate the display image for some pendant 56 orientations, such as converting from sitting on a table with the cable 58 behind to hanging on a wall hook with the cable 58 below.

Figure 4:
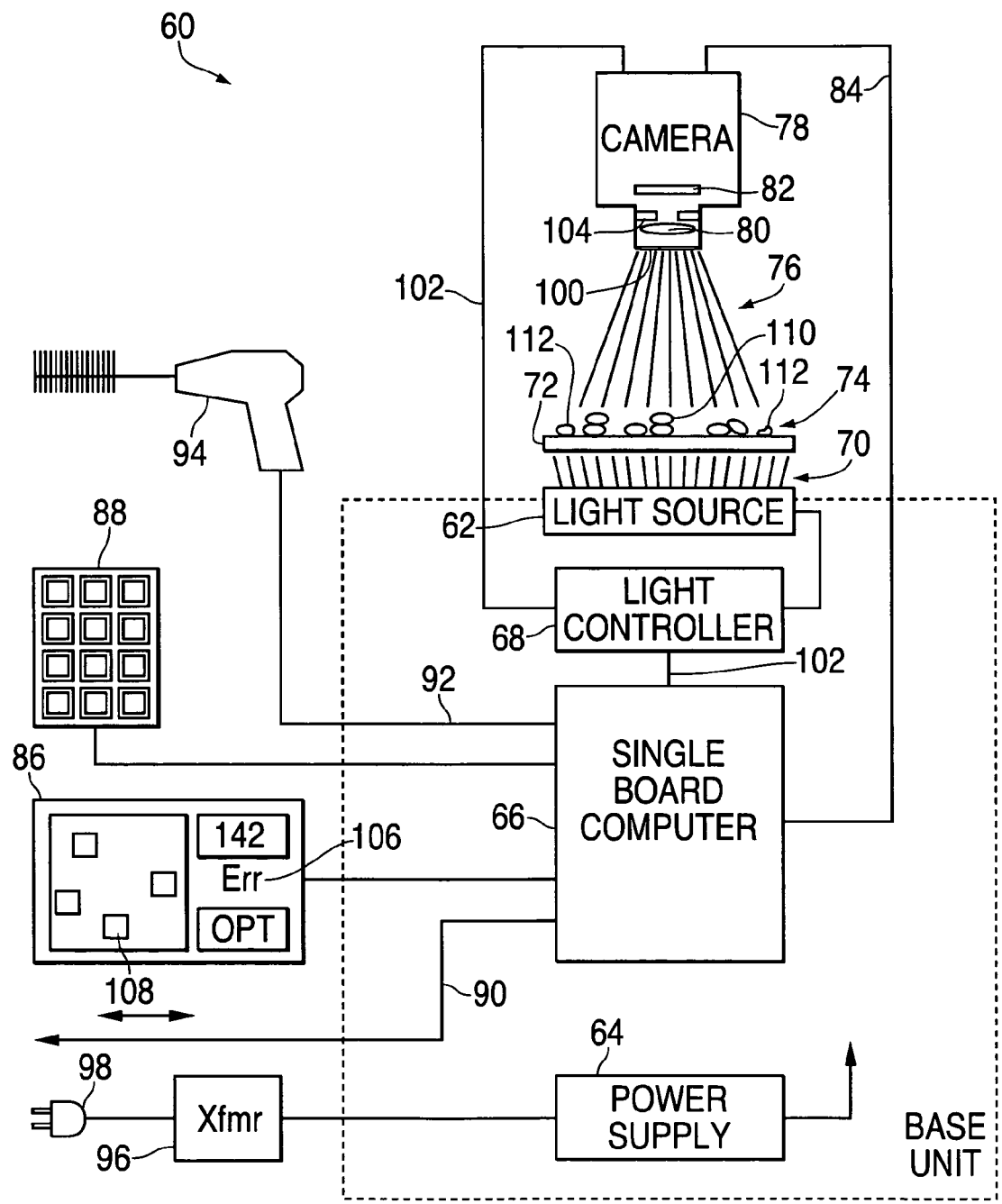
FIG. 4 is a block diagram consistent with a method according to one embodiment of the invention.

FIG. 4 shows a counter 60, in block diagram form, having some of the functional elements indicated in the foregoing pictorial figures. The counter 60, like the counters 10 of FIG. 1, 32 of FIG. 2, and 52 of FIG. 3, can take the form of a single, substantially unitized apparatus. As shown in the block diagram, an illumination source 62 powered from a power supply 64 with timing controlled from a processor module 66, and in some embodiments including a discretely identifiable illumination source power control module 68, emits radiation 70, such as infrared light, that passes through a stage 72 and is blocked in part by subject units 74. A portion of the unblocked radiation 76 impinges on a camera 78, functioning as an image acquisition component, whereof a focusing mechanism 80 such as a pinhole or a lens may be used to place an image in the form of silhouettes of the units 74 on a detector 82, functioning as a machine vision transducer. The detector 82 couples the image in a transferable format such as a digital data stream to the processor module 66. The image is coupled via a power and communication link 84 such as a power-carrying electrical data signal cable or a combined power cable and fiber optic link in the embodiment shown. The processor module 66 further interprets the camera 78 image to generate a count of units 74 at periodic intervals. This count may be presented on a display component 86, and may be updated at a rate determined by a control routine stored within the processor module 66 or determined by input from a user, for example.

Additional functions of a counter 60 may include provision for local control input using a keypad 88. Such a keypad 88 may in some embodiments have the form of a touchpad overlay, that is, an array of substantially transparent pressure transducers or a functionally equivalent device, providing output usable in place of pushbutton switch contacts, with the touchpad superimposed on the display component 86. Functions in some embodiments may also include one or more external communication links 90, whereby, for example, the counter 60 may operate a system or the system may operate the counter 60, as appropriate for an application. Such relationships are commonly described as master and slave; as appropriate, a counter 60 may selectably perform either master or slave function or may be limited to one or the other.

In some embodiments, another included interface 92 may support an optical reading device, such as a barcode scanner 94. Power for operating the counter 60 may be self-contained, using some combination of replaceable, rechargeable, and/or solar batteries included in the power supply function 64, may be externally powered using direct or indirect (such as from an external transformer 96) feed from a premises wiring plug 98, or may be otherwise energized, as selected for a particular use.

The illumination source 62 may, in some embodiments, provide electromagnetic energy in the form of infrared light at low average intensity and with a time-controlled, low duty cycle emission envelope. Where so implemented, the radiative intensity can be "strobed," that is, pulses of light can be emitted having a selected rate, duration, and emission intensity envelope. In strobed configurations, overall emission may be substantially lower than would be the case were the illumination source 62 operated continuously at an emission level compatible with a particular camera 78. This may, in some embodiments, allow a high enough illumination level for efficient operation of the camera 78, while lowering the net power radiated and/or conducted downward into any electronic devices housed below the source 62. This can in turn reduce component stress, extend component life, reduce overall power consumption and power supply size and weight, and/or reduce tendencies for susceptible components to drift in value with temperature. Strobe capability may further allow operation without a cooling/air distribution fan in some embodiments.

In some embodiments, a planar array of infrared light emitting diode (LED) devices, substantially matched for uniformity of emission intensity and wavelength, and affixed below the stage 72, may be used to establish a diffuse illumination source 62. In other embodiments, a single, possibly higher intensity device, effectively a point source, the emission from which is distributed and directed by a lens, a focusing reflector, or a combination of such accessories, for example, may be used as the illumination source 62.

Light having a wavelength outside the infrared portion of the spectrum may be used in some embodiments. Illumination may likewise be of multiple wavelengths, such as white light. One or more downward-directed illumination sources, such as, for example, ambient room light or a second light source at camera 78 level (shown also as source 116 and camera 118 in FIG. 5), may permit one or more attributes of the units 74 in addition to quantity and/or shape to be detected, such as color, transparency, imprint symbols, and the like. In embodiments having a plurality of light sources and/or a source emitting a plurality of colors, reflected light in addition to or in place of silhouette illumination may be detected. Such capability may in some embodiments permit or enhance detection of flawed or incorrect units in a sample, for example. The camera 78 of FIG. 4 may acquire a reference brightness level when the stage is empty, then use the reference level to establish contrast levels during counting.

Illumination using energy other than infrared and visible light may be used in some embodiments. Within the electromagnetic (EM) spectrum, microwave radiation (i.e., EM waves longer than infrared) may provide adequate resolution in some embodiments, while ultraviolet light (UV, EM above visible) or x-rays may be usable in other embodiments. Acoustical energy, such as ultrasonic emission, can have wave dimensions and power levels permitting acquisition of an image of a stage whereon a number of countable units are placed, with sufficiently high resolution and image refresh rate to meet system needs. Still other imaging methods and media may likewise be applicable in some embodiments.

Contrast between the appearance of the surface of the stage 72 and of the units 74 being counted may be further enhanced, particularly in a high ambient light level or broad-spectrum light environment, by positioning one or more filters 100 having properties suitable for limiting light impinging on the detector 82 to spectral elements of interest. For an infrared source 62 illuminating a detector 82 that is insensitive and thus self-filtering for spectral elements longer in wavelength than the far infrared, an infrared low pass filter may be used, while for embodiments wherein multiple spectral elements are to be detected, combinations of low pass and/or band blocking (notch) filters may be used. It is to be understood that a single filter 100 combining multiple notch filters and bandpass or lowpass filters may be used in some embodiments.

In embodiments using strobing, synchronization by a sync signal line 102 may be directed from a relevant circuit element such as the processor 66 or the power control module 68 to the camera 78. Applying the sync signal to the camera 78 allows image acquisition to be synchronized to the availability of light from the source 62. The strobe function can reduce energy flux and gradient into the units being counted, thereby impeding degradation for some heat-sensitive, light-sensitive, or short-life medications or packaging configurations.

Some light sources 62 provide a substantially uniform areal brightness distribution, and further provide rapid turnon and turnoff of emission. Other light sources 62 may provide illumination compatible with data acquisition properties of specific types of detectors 82. For example, a detector 82 may intrinsically perform raster scanning over an image area, that is, acquire data from an array of picture elements by sequentially reading instantaneous brightness values from the elements, getting a succession of values across a single row of the detector 82, then advancing to the next row and repeating the process. For such a detector 82, only an area of the source 62 optically focused on the portion of the detector 82 being read need be activated, further reducing power consumption and emission. For another type of detector 82, the entire detector surface may be illuminated and may capture an image in the form of electrical charge on discrete picture elements, after which the image may be transferred by a process such as "bucket brigade" charge transfer with the relatively low brightness of reflected ambient light continuing to impinge. For this latter type of detector 82, a uniform illumination pulse over the surface of the source 62 may be used. Other detector 82 technologies may dictate still other modes of operation of the source 62.

Light emission may be substantially random in phase and direction for some illumination sources 62. For source 62 embodiments having comparatively uniform emission distribution over the surface of the source 62, or having comparatively uniform areal intensity striking the camera 78, signal processing may be simplified compared to signal processing required for sources 62 having pronouncedly nonuniform emission. In embodiments having less uniformity, either over the source 62 surface or over apparatus lifetime, a baseline surface mapping can be established and refreshed periodically as appropriate, to precompensate for source 62 variation. Furthermore, in some embodiments, adjusting emission intensity or emission pulse duration can be used to regulate signal input level into the camera 78 to remain within a range. In some embodiments, the camera 78 may allow detector 82 sensitivity to be controlled over portions of the image area of the camera 78, so that precompensation for source 62 areal intensity variation may be performed prior to providing the image information from the camera 78 to the processor 66. Similarly, impinging light may be regulated or switched using a mechanical or electrochromic shutter 104.

Figure 5:
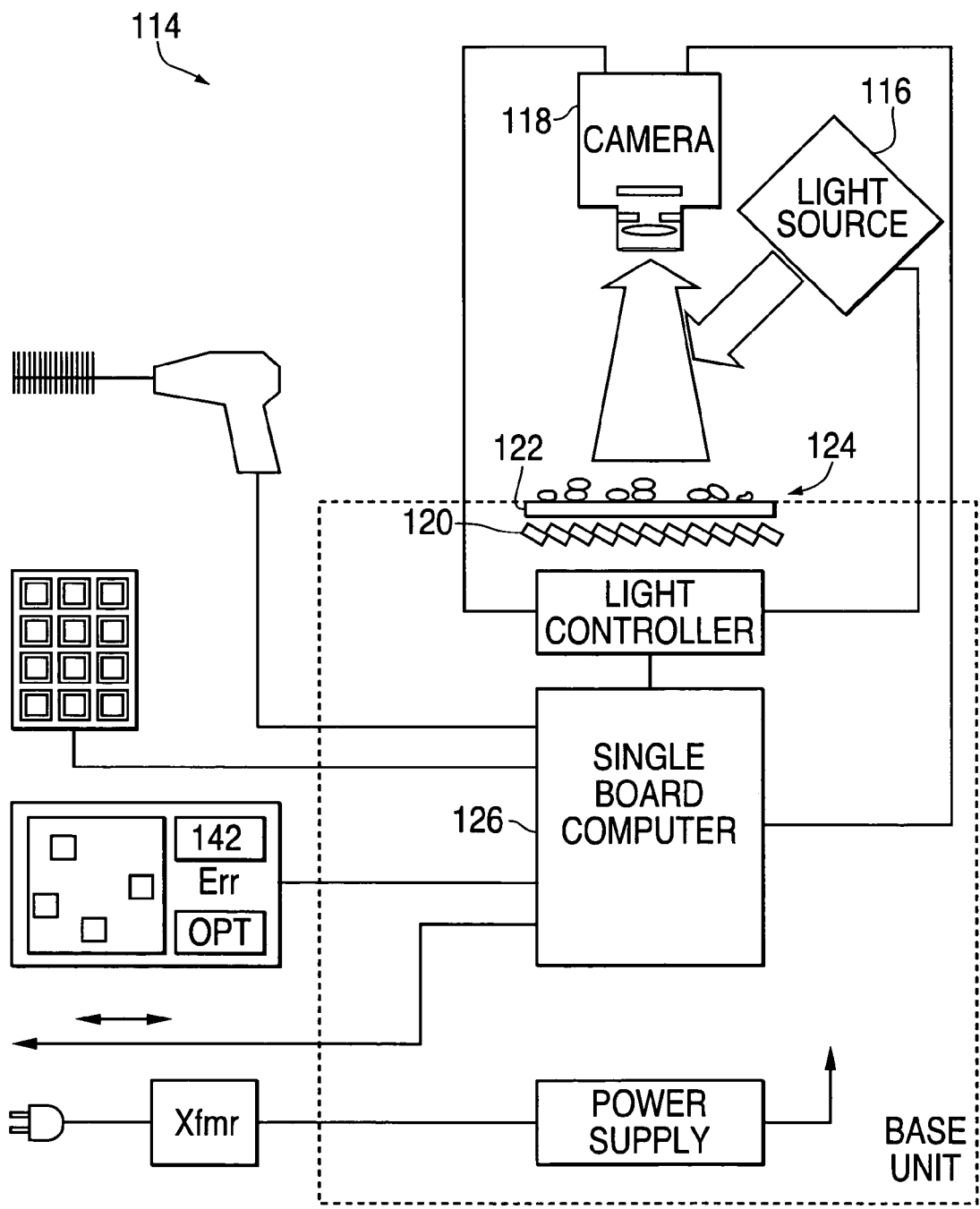
FIG. 5 is an alternative embodiment in block diagram form.

FIG. 5 is an example of another embodiment 114, wherein a source 116 is positioned substantially at the level of the camera 118, for example. Such a source 116 may be diffuse, that is, may have largely uniform and low energy density emission over a relatively broad surface, or may approximate a point source, that is, may emit with comparatively high energy density from a small spot. Each such configuration, as well as intermediate forms such as multiple discrete spot sources, may be superior in conjunction with particular imaging methods.

For some embodiments, a passive reflector 120 beneath the stage 122, which may be focused, can be used to reflect light from the source 116 back to the camera 118, with deflection or diffusion of the light by the units 124 providing contrast. The reflector 120 in FIG. 5 is a collapsed type, such as a metalized negative Fresnel lens; other configurations are feasible as well. The size shown for the reflective components of the reflector 120 is larger in FIG. 5 than in some embodiments, with the understanding that finer scale reflective components can more readily establish a low-profile, accurately focused mirror, while components comparable in scale to the units being counted may be preferable for other embodiments. For still other embodiments, a stage or substage surface that largely absorbs or deflects the wavelength of the source 116 can be used, so that the units 124 are seen by the camera 118 as brightly lit against a relatively dark background. The last embodiments could require an adaptation of the processor 126 algorithm to account for discrete specular reflections from gel capsules, coated pills, and other shiny unit surfaces, for example. Similarly, variations in reflectivity of subject units may require added camera bit depth or processor algorithmic complexity in some such embodiments. Embodiments using reflectors 120 beneath the stage 122 could be unsuitable for counting some types of reflective units unless the position and other attributes of the illumination source were arranged to accommodate such uses, such as by offsetting the source 116 with respect to the central axis of the camera 118 field of view.

In still other embodiments, comparable resolution and speed may be achieved using a narrow, directable spot of light, such as a laser beam within the source 116, directed over an area using a Micro Electro Mechanical System (MEMS) or another beam steering system. In such an embodiment, the beam is scanned over the stage, and the scan result is detected by a "camera" 118 that can be as simple as an unfocused single-element photodetector. Such an embodiment may use silhouette, reflection, or combined imaging, and may use a plurality of light sources of different wavelengths. The analytical algorithm for evaluating an image so acquired, discussed below, may also be adapted, such as by performing a low-resolution scan with the beam to find unit candidates, then edge tracing or rescanning at higher resolution to evaluate areas of interest. The process may further vary spot size.

In some embodiments, an areal counting function may be executed repeatedly at selected intervals, with count results on the display 86 of FIG. 4 then updated, for example after completion of each count. For sufficiently rapid count intervals, such as multiple times per second, the update rate may appear to a user to be essentially continuous. As an operational consideration, such a process may allow a dispensing agent to pour out units onto the tray 54 of FIG. 2, for example, until an approximately correct count is seen on the display 86 of FIG. 4. The agent can then verify that no piles obscuring observation are present on the tray 54, and can redistribute the units if necessary, with the results presented effectively instantaneously at each step.

In some embodiments, in addition to providing a count of discretely identifiable units interrupting illumination over several consecutive scan lines at a broadly uniform position with reference to a first end of the scan lines, a processor 66 may provide an inspection function. That is, the processor 66 may be configured to anticipate the approximate areal coverage or "blob size" of the units being counted, and to determine for each discretely identifiable unit whether the size generally corresponds to that expected for such a unit, in consideration of a range of orientations of the unit. Thus, for example, where unit size is too small to be consistent with any anticipated orientation for that unit, the unit may be tagged as possibly chipped or a fragment. Similarly, where a unit occupies a large enough region but shows a shape that is nonuniform, exceeds a stipulated range of rates of curvature, or otherwise exceeds geometric model limits, the unit may be tagged as possibly defective. Such information may be presented on the display 86 of FIG. 4, variously in text form 106 or as a graphical image 108 showing the general location of a suspected fragment 112. Fragments below a stipulated size may be ignored in some embodiments.

Compound element images may be identified as multiple discrete units through application of geometric pattern matching functions. Where predefined or other geometric patterns can be detected within a compound element image, the patterns can be classed as units within the image. The patterns defined by these units may be, in effect, subtracted from the image, leaving the areas obscured by the patterns indeterminate, i.e., classed as neither illuminated nor part of the silhouette image. The remaining image may then have the pattern matching function further applied, and other patterns may in turn be identified. Such an iterative process may in some embodiments permit compound images to be partitioned and counted with acceptable accuracy, and may further allow identification of broken pieces of units. The process may further identify and tag extraneous items—that is, items not having geometric patterns corresponding to units or combinations of units—with these omitted from a count. This process may be termed discrimination between patterns.

In some embodiments, the processor 66 may identify touching or overlapping units, allowing counting of units within multi-unit groups in some configurations and directing an agent to scatter such groups where likelihood of accurate counting is unacceptably low. It will be understood that a limit on such capability may occur where units such as flat-faced pills—squat cylinders—are stacked 110 substantially perpendicularly to the local view axis of the camera 78, as shown in FIG. 4. Such configurations may reduce the efficiency of the counting machine despite use of procedures outlined above. Additional procedures such as the one discussed below may restore efficiency.

In some embodiments, the processor 66 acquires a unit count over multiple sample cycles, during which interval the agent may add units to the stage 72. The processor 66 compares unit counts in successive sample cycles, with successive counts typically increasing in value. Where a final count target is known, the agent may need to add or remove units after a stable count is established. Under some conditions, a count may be observed to decrease anomalously, which may result from stacking 110. A processor 66 detecting such a condition may present a message to the agent directing that the units be spread, and may further indicate one or more regions on the stage 72 as appropriate.

Figure 6:
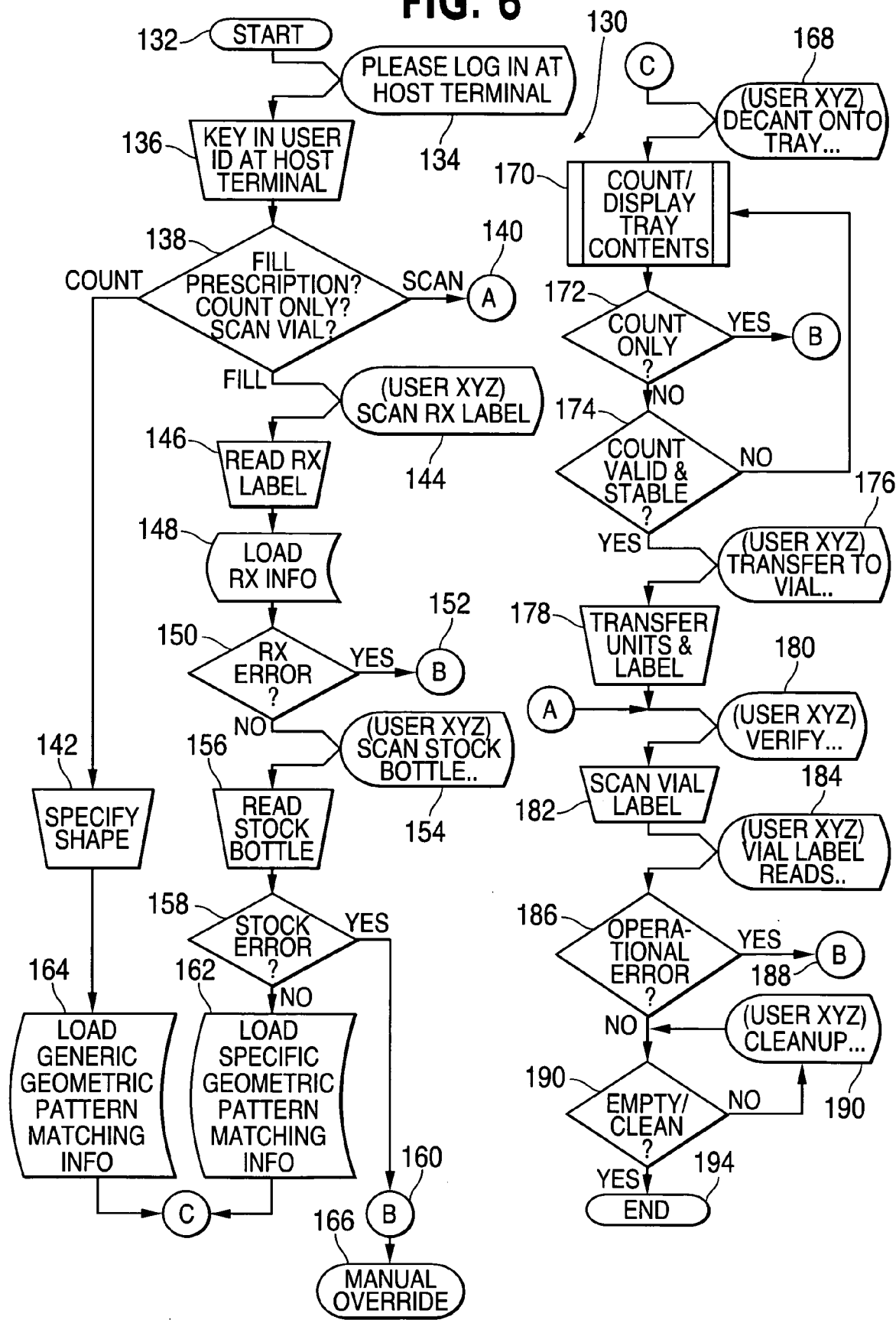
FIG. 6 is a flowchart indicating a procedure followed by a counter according to one embodiment of the invention.

FIG. 6 shows default overall signal flow according to one embodiment of the invention. After initialization 132, an agent is prompted 134 to perform a login function 136. Note that in a standalone system configuration or a configuration wherein the counter in use is the master, the term "host terminal" may apply to the counter itself. For such applications, the counter can support digital data entry, such as for login, as a function of the display 86 and of the touchscreen or keypad 88 of FIG. 4. For other embodiments, a host separate from the counter may provide login confirmation input through the communication link 90 of FIG. 4.

Once an agent (here, USERXYZ) is recognized, task options 138 may include, in some embodiments, filling a prescription (Rx), performing a count on units not associated with a prescription, and scanning an existing prescription vial. Where the task is limited to scanning an existing vial, count processes are bypassed, and execution jumps 140 to a later node in the routine. Where the task is to count units, indication of unit shape may be provided 142 by the agent to the counter 130. Where the unit shape is known, the agent can select the shape from a menu referencing a database, for example. Where the unit shape is not available from a resource, the shape can be specified for the task by defining a geometry in terms of curvature, diameter, and the like, defaulting to a nominal shape and size, or another method.

Where the task is to fill a prescription, the counter can prompt the agent 144 to scan 146 a reference document such as a previously prepared prescription label. For some embodiments, a method for scanning may use the bar code scanner 94 of FIG. 4 to read a bar code printed on the label. In other embodiments, the scan process may involve keypad entry of a reference number, or may require entry of text such as prescriber's name, formulation, quantity, and the like, with a label being printed, as a response to the input, using a printer external to the counter.

After the prescription label information is acquired, associated information may be loaded 148 from a reference resource external to the counter, using, for example, the external communication link 90 in FIG. 4. In other embodiments, some or all of the associated information may be contained in a database internal to the counter 10. The loaded information may be evaluated for some classes of errors 150, such as an unauthorized or already-filled prescription, and, if defective 152, brought to the attention of the agent 160, 166. Where the information is proper, the counter can prompt the agent 154 to scan 156 a stock bottle (a bulk storage container for a prescription), using the method previously used 146 for the label. If the stock bottle is incorrect 158, the agent is directed to intervene 160, 166; if correct, geometric pattern information for the units may then be loaded from a database 162, where the database information is maintained within or external to the counter. At this point, the generic counting option and the prescription filling option paths from step 138 converge, with a geometric pattern not associated with a prescription loaded 164, and the procedure continuing to the count phase.

The agent is then directed 168 to decant the units into the tray, after which the count function loop described in FIG. 6 is invoked 170. If the procedure is only a count 172, then the loop may be limited to a single execution pass. If not, the loop may instead monitor the decanting process by repeatedly executing the counting process 170 until a valid count is achieved 174, discussed in detail below. To complete the procedure, the agent is directed 176 to transfer the counted units (and the label, if not previously done) to the final vial 178, then to verify 180 by rescanning the label 182, which is then displayed 184. If a mistake has occurred 186, the agent is directed 188 to intervene 160, 166; otherwise, the scan surface is examined for visible contamination 190 and the agent may be prompted to clean the scan surface 192, after which the procedure is finished 194.

Figure 7:
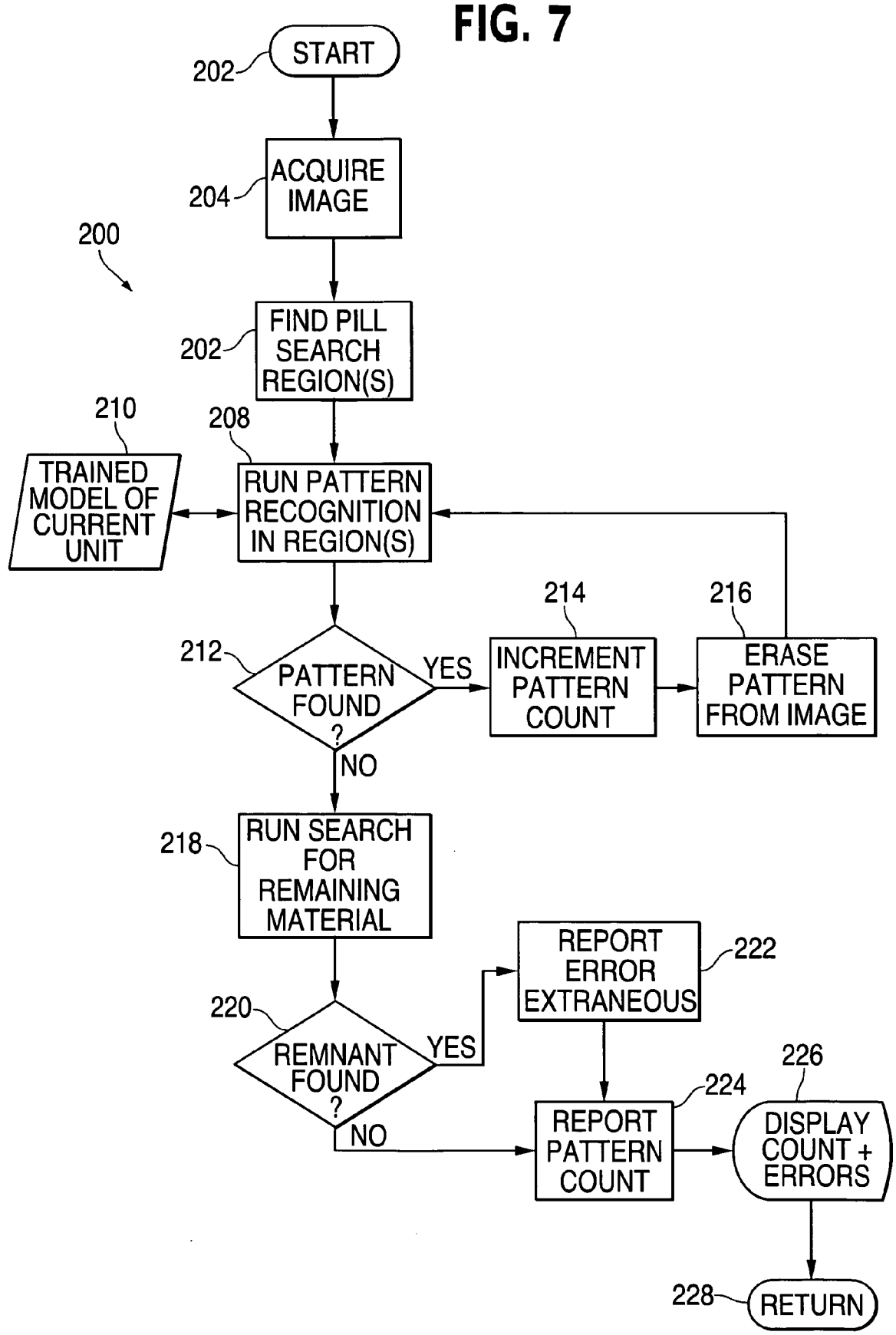
FIG. 7 is a flowchart indicating a counting procedure according to one embodiment of the invention.

FIG. 7 shows the process for acquiring a unit count 200 based on the content of a scannable tray. As indicated in the flowchart of FIG. 6, a stock bottle reading 156 or a specific or generic shape definition 142 allows geometric pattern matching information 162 or 164 to be applied to a counting task 170. As is further shown in FIG. 7, the count function 200 is initialized 202 and a tray image is acquired 204 for the routine.

Referring again to FIG. 4, in some embodiments, the image acquisition process provides a timing signal on a signal line 102 both to activate the illumination source 62 and to initialize the camera 78 to perform a raster scan over the stage 72.

Each picture element (pixel) in the field of the camera 78 is converted from a light intensity level to an electrical signal level by the camera 78. The signals, which may be analog in form, are then digitized, either intrinsically, internally to the camera 78, or within the processor 66. In some embodiments, the digitized image may have single-bit depth, meaning that each pixel is blank or non-blank, i.e., above or below a brightness threshold. Each such image in the processor 66 may then be an array of 0's, for example, representing the unblocked source 62, and 1's, representing the silhouettes of the units 74 and any stray material. In other embodiments, multiple colors or shades of gray may be acquired, using one or more light sources 62. Images then require multiple bits per pixel: two bits to represent four discrete levels or colors, four bits to represent sixteen, and so forth. Such additional information may enhance system capability, such as by allowing pixels to be classed as partially on an edge of a unit rather than entirely on or off the edge, affording "subpixel" image resolution.

Returning to FIG. 7, the image acquired 204 is evaluated 206 for searchable (non-blank) regions. For example, bright (infrared) illumination, detected substantially uniformly over the area of the illumination source (equivalent to the stage or a background field), and potentially further restricted by identifiable edges of a tray resting on the stage, implies that the background field is empty. If one or more contrasting image elements exist in the background field, then search regions proximal to the contrasting elements may be added to a list.

A pattern recognition routine may then be executed 208 over the search regions, using as a reference a "trained model" 210 of units to be counted, corresponding generally to the specific geometric pattern 162 of FIG. 6. According to one imaging technique, a model can use a pattern of image elements having a particular extent and line-by-line relationship, implying area coverage and contiguity. According to another imaging technique, a curve-fitting algorithm can detect the locations of the light-to-dark boundaries of a pattern within a search region, and then compare these to a sequence that would obtain from an ideal point set for the model. If the aggregate error is low enough, the pattern may be affirmed as agreeing with the model. Alternative modeling strategies consistent with other techniques may be used. An untrained model may be fully effective for round, flat pills, for example, if it is assumed that the pills will be largely separated from each other, so that each pattern within a search region is distinct and supports identification. A trained model, by contrast, may anticipate multiple angular orientations, known non-circular unit shapes, and proximity between units that may leave portions of units obscured. The trained model may be a geometric approximation based on vendor literature, or may be based on images acquired using a counter according to the inventive apparatus and method, tasked to execute a training routine and add the trained model to a database.

Once a pattern is detected 212, a counter function maintaining a running count of patterns found can be incremented 214, and the image elements comprising the found pattern can be blanked 216.

The pattern recognition routine may include rejected regions as well as found patterns. That is, for a sequence that does not satisfy the criteria for a trained model, a local area or a search region can be set aside and the pattern recognition routine 208 run on any remaining search regions within the bounded background field, until all "easy" patterns have been found 212. Previously rejected search regions may be revisited, and may reveal additional patterns after blanking other patterns. Ultimately, no further patterns will be found 212. There may remain regions that are neither wholly blank nor valid. These regions may be searched 218, and may contain remnants according to criteria of the trained model. If such remnants are found 220, a report 222 may be generated, which report 222 may include location information for each such finding. Whether there are remnants or not, a report of the number of found patterns can be generated 224, and the results of the count routine can be presented for display 226, ending the procedure 228.

After completion of a single pass through the count routine 200 of FIG. 7, the counter can be configured to halt, or can repeat at a chosen rate as shown at step 172 in FIG. 6. Where the count sequence is repeated, for example at a high rate, an agent can pour units onto the tray and observe the achieved count in near real time. Where errors are indicated, the agent may manually redistribute units, and may respond to detection of suspected remnants, for example, by removing them and observing the refined count.

It is to be understood that in some embodiments, the count function may be run at a rate approximating the fastest rate of which the apparatus is capable, irrespective of conditions, while in other embodiments, a tray determined to be empty may be examined at an infrequent rate, or may be ignored until an execute command is sensed. The latter embodiments can render the counter largely inert while awaiting the start of a processing procedure such as those presented in FIG. 6, and can thereafter minimize count rate once a valid final count has persisted for a time interval. Similarly, variable counting rate may be used in event of significant errors, such as appreciable numbers of fragments, units so piled as to be uncountable, presence of shapes inconsistent with the database information for the units, or another operational problem, to slow or stop execution and present error signals.

Figure 8:
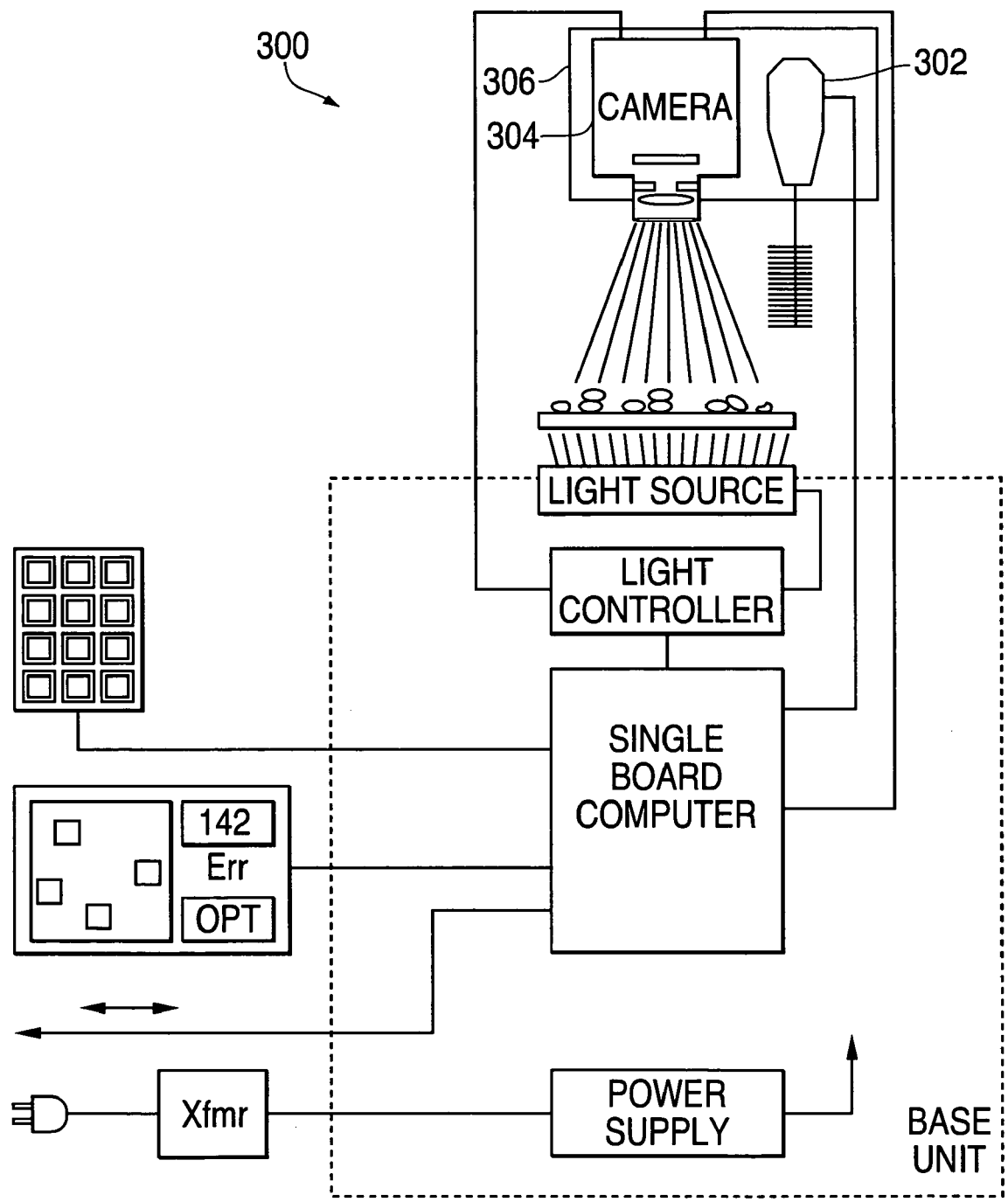
FIG. 8 is an additional alternative embodiment in block diagram form.

FIG. 8 shows the block diagram of FIG. 4, further adapted by integrating into the apparatus 300 a data acquisition device 302. A device 302 generally similar to the bar code scanner 94 shown in FIG. 4 can be integrated into the head 304 containing the camera 306 in some embodiments. In some embodiments, the data acquisition device 302 can provide one- or two-dimensional bar code scanning by moving a self-supplied visible light source, such as a steerable laser beam, over a field such as an agent identification card or an encoded reference number on a stock bottle. The sequence of light intensities reflected from the field can then be sensed and interpreted as a string of data elements that encode selected information. The information may include that described above in discussion regarding FIGS. 4-7, such as prescriber and product codes, as well as security information. In other embodiments, the light source may be infrared, for example, or the scanning process may use a radio or magnetically coupled signal to acquire data. In some embodiments, the scan function may be performed by components also used for image acquisition.

Figure 9:
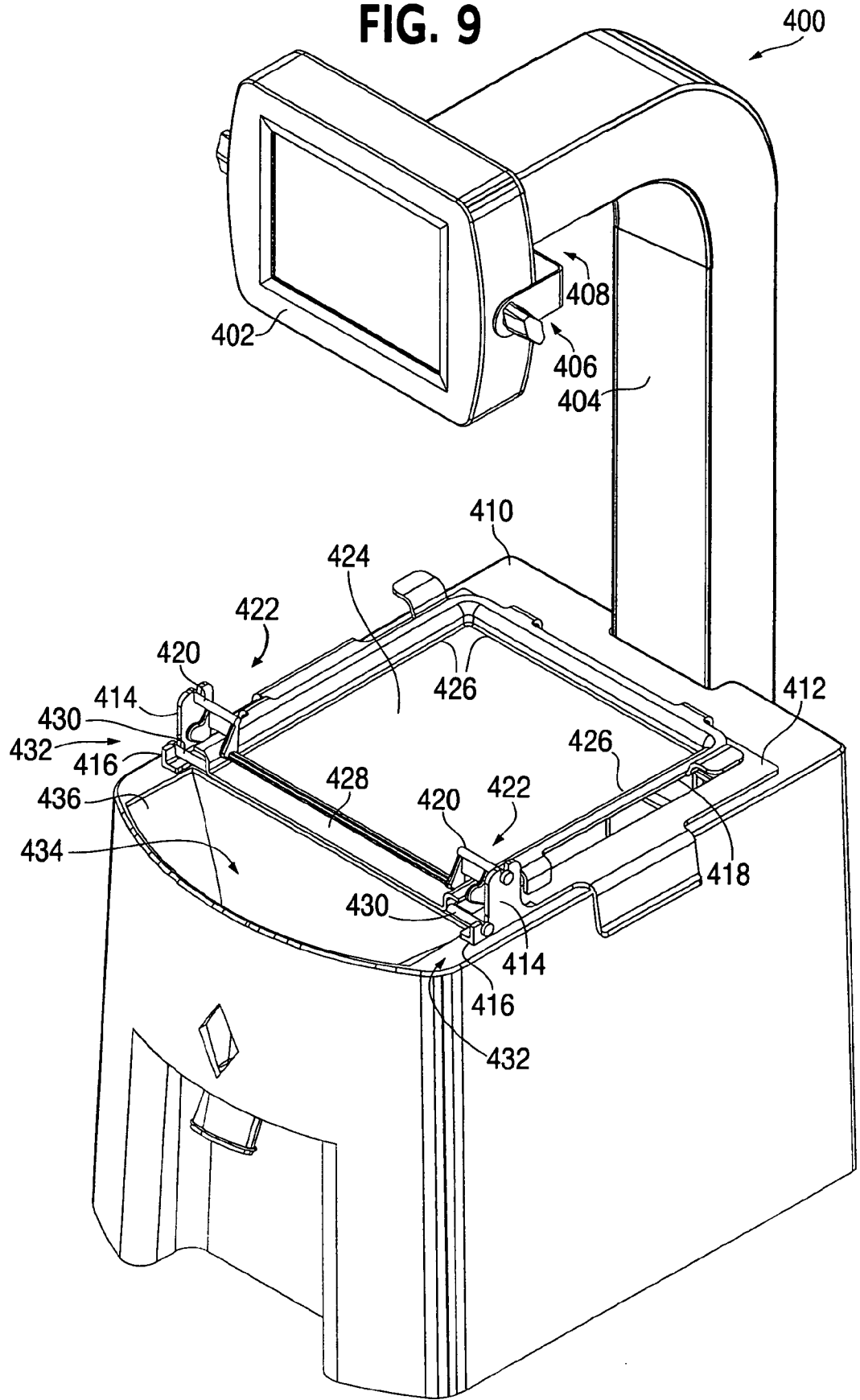
FIG. 9 is a perspective view of an additional alternative embodiment of the invention.
Figure 10:
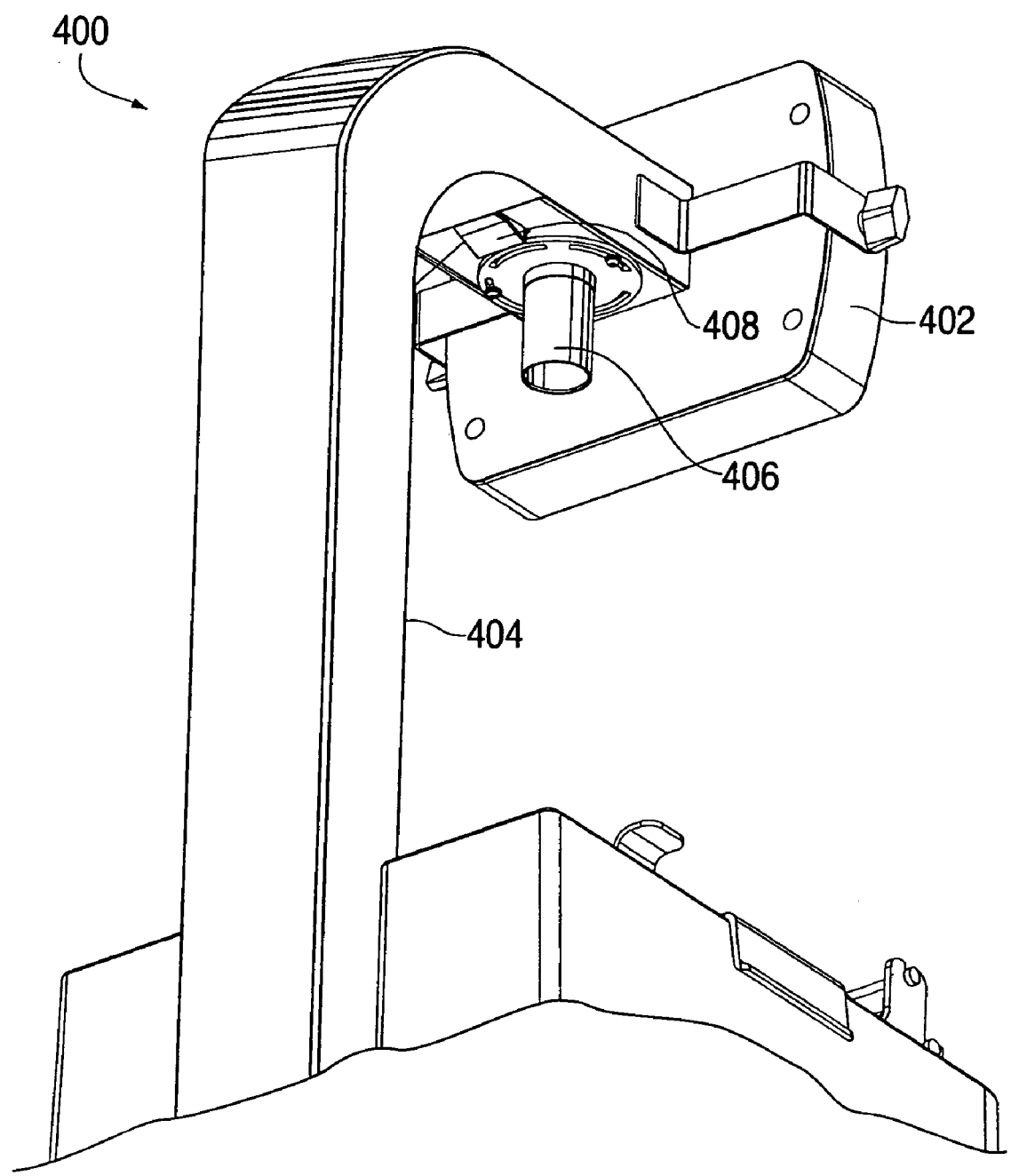
FIG. 10 is an additional view of the embodiment of FIG. 9.

FIG. 9 shows a first perspective view of still another embodiment of a counter 400. In this embodiment, a display/user interface 402 is positioned at the top front of a principal support arm 404. A camera 406 and a scanner 408, visible in FIG. 10, are located on the arm 404 behind the display 402. Returning to FIG. 9, a base 410 has affixed thereto an adapter 412 having a first pair of pivots 414 and a second pair of pivots 416. First pivots 414 locate a tray 418 having a first pair of hinge pins 420 mated to the first pivots 414 to form a first hinge mechanism 422. Tray 418 has a floor 424 and three walls 426. Second pivots 416 locate a stop bar 428 that forms the fourth wall of the tray 418, with a second pair of hinge pins 430 mated to the second pivots 416 to form a second hinge mechanism 432. The base 410 further includes a guide chute 434.

Location of the display/user interface 402 with respect to the base 410 involves considerations of ergonomics as well as optical geometry. In the embodiment shown, the display/user interface 402 is positioned substantially as close as possible to the camera 406, which in turn is positioned substantially directly above the center of the base 410. In other embodiments, including, for example, those shown in FIGS. 1-3, other locations for the display/user interface 402 may be selected by those skilled in the art, in view of such considerations as display visibility and touch-screen actuation convenience.

As further shown in the embodiment of FIG. 9, an auxiliary chute 436 can be positioned within the guide chute 434. This arrangement permits the tray 418, the stop bar 428, and the auxiliary chute 436 to be the only components of the counter 400 that ordinarily come into physical contact with units being counted. By configuring these components to be readily removable, such as by lifting off the adapter 412 and withdrawing the auxiliary chute 436, the counter enables an agent to substantially completely isolate countable units of highly incompatible types. For example, capsules containing a medication in a finely divided form may have traces of the medication on the outside of the capsules, wherefrom particles could fall onto the tray 418 during counting. Other tablets or capsules counted subsequently could pick up the particles in quantities sufficient to constitute cross-contamination. By allowing the agent to remove and thoroughly clean the entire contact path with relative ease, the counter 400 configuration of FIG. 9 can be made usable for essentially any types of units. Moreover, multiple sets of contact path components can be interchanged for convenience in processing large numbers of prescriptions during peak periods, for example. Where specific considerations so dictate, contact path components can be treated as disposable.

Figure 11:
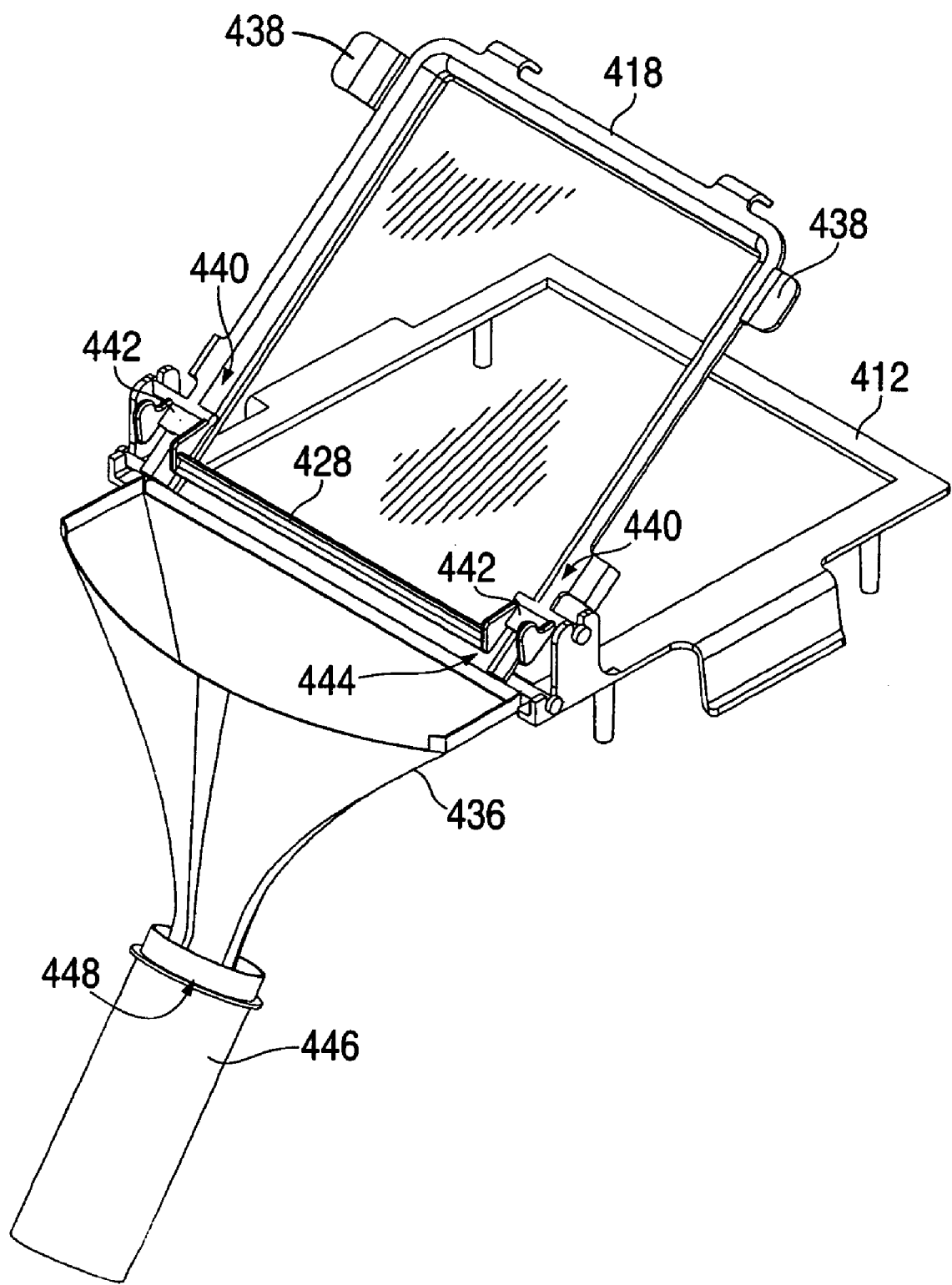
FIG. 11 is an additional view of the embodiment of FIG. 9.

FIG. 11 shows a second perspective view of the adapter 412 and the contact path components 418, 428, and 436 as employed in completing a counting operation and transferring the units from the counter 400. Here, the tray 418 is shown tipped up, such as by the agent grasping and raising one of the lift tabs 438, with the motion of the tray 418 transferred to the stop bar 428 by cams 440 on the tray 418. The cams 440 bear against flaps 442, shown in this embodiment as integral with the stop bar 428. The joint tilting of the tray 418 and the stop bar 428 opens a gap 444 in the perimeter, leading to the auxiliary chute 436. It is to be understood that, in the embodiment shown, the stop bar 428 is free to swing back to a closed position when the tray 418 is lowered to its rest position; in other embodiments, a spring or another cam arrangement can impel stop bar 428 motion. A receiver bottle 446 can be positioned at the exit portal 448 of the auxiliary chute 436, for example by an agent holding the receiver bottle 446 in hand.

It is to be understood that the hinge embodiment presented in FIGS. 9-11 is one of many possible arrangements. For example, mating depressions and protrusions on the respective components can provide hinge function in lieu of identifiable hinge pins and pivots, or separate hinge pins can be used along with bearing fixing holes and/or attachment points in each part to provide hinge function. In other embodiments, multiple components can be molded as a unit from a material sufficiently resilient that the hinge functions can be realized using so-called self-hinges. That is, allowance for repeated bending of the material, such as at purpose-made locations, i.e., self-hinges, can enable the required range and ease of motion without recourse to multiple parts. Similarly, discrete components can be connected with resilient hinge material to accomplish comparable functionality. Selection of one or more of these arrangements or others that will occur to those proficient in the relevant arts may depend on the requirements of a specific embodiment.

The foregoing process may be compared to the process required for an unpivoted tray, as shown in FIG. 2, wherein the agent lifts the tray from the stage, tilts the tray to direct the units into a corner of the tray, then further directs the units into a receiver bottle. It is to be understood that a unit handling arrangement using a pivoted tray and an associated chute may be adaptable to the embodiments of FIGS. 1, 2, and 3.

A greater or lesser security capability may be used in various embodiments. For example, positive identification of an agent bearing a scannable badge may be appropriate, whether to maintain audit trail on controlled substances, to monitor employee productivity, or in view of another consideration. To cite another example, stock bottle bar codes may be associated with unit shape definitions in a database. Positive confirmation of unit shape while counting may assure safety and quality control as well as maintaining audit trail. These or other security aspects may be relevant to particular embodiments.

Various features may be included in the inventive apparatus to augment security. The features may include, for example, control of software configuration modification, so that downloading an altered database of geometric data defining unit shape requires a password or other, more rigorous identification. Stock bottles may be provided with geometric data embedded in a bar code, so that no separate database is required, and the bottle and its contents are logically linked. Regarding technology choice between one-dimensional and two-dimensional bar codes, it is to be understood that the embedded geometry describing a specific unit may be more readily implemented in embodiments employing the longer sequences possible with two-dimensional bar codes.

Other features potentially desirable in some embodiments include a requirement for a long and/or encrypted agent badge code, embedment within the agent badge code of one or more biometrics such as a scan of relative finger length profile, a requirement that a password be changed periodically, or a combination of these and other security measures. It is to be understood that processor-based security functions associated with a counter may include procedures to acquire affirmative information, such as badge code decryption and confirmation, polling of individual subassemblies to acquire and examine condition reports, transmitting test codes and verifying responses, and the like. Thus, an indication that counter security status is good can be derived from an affirmative security test sequence that may be extensive in some embodiments.

Further, negative events may negate a security good indication. For example, a loss of a power good signal from a power supply may generate a processor interrupt for system shutdown without data loss, which can be usable in embodiments where prior system state is needed during restart, for example. Similarly, specific security related or operational negative events may be detected, such as removal of a closure seal on the counter, timeout of a watchdog counter, overtemperature detection from a thermal sensor having go/no go state switching, and the like. Identification of a recognized agent may be viewed as an affirmative security procedure enabling operation, while touching a "standby" button on a touchscreen or absence of agent input, including change in count or position of units on the stage for a stipulated period, may be viewed as a negative security event initiating disablement of operation. Where appropriate, a security bypass function may be applied to override a disablement function and allow operation of at least one function without direct access to the security sequence required for normal operation. Criteria for such bypasses may be developed for individual embodiments.

Alternate embodiments may employ substantially the same counting algorithm as presented in the discussion of FIGS. 6 and 7, using imager heads that may not be fixed and oriented downward toward horizontal stages. Such embodiments, using ambient light, scanning lasers, or pulsed, diffused infrared, among other illuminating radiation sources, may count units at various distances from the imager heads. Applications are not limited to prescription fulfillment, nor to counting functions. In some embodiments, a principal use can be detection of defective frangible items, such as in light bulb quality control monitoring a conveyor belt. In still other embodiments, law enforcement may find uses in counting crowd populations or automobile traffic. Similarly, detection of burned-out streetlights from imagers mounted on cell phone towers, or counting whitecaps from imagers borne on aircraft as an indication of wind speed, may be feasible.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

What is claimed is:

1. A machine-vision-based counter for counting discrete units, comprising:
    an image acquisition component configured to detect light having at least one wavelength, wherein the light provides discrimination between a background field and a quantity of imageable units located at a distance from the image acquisition component, and to provide, as an output, data representing the background field and the units;
    an image processor configured to receive data from the image acquisition component, and further configured to interpret the data as a field image whereon are superimposed a quantity of countable units;
    an operator interface component configured to present a count result output from the counter and to accept at least one command input to the counter; and
    a counter controller configured to manage at least the image acquisition, image processor, and operator interface functions of the counter;
    a first light source, wherein the first light source illuminates at least an area associated with the background field, wherein the first light source has a first spectral component, wherein light, emitted from the first light source and directed to units positioned to be detected by the image acquisition component, is thereafter directed at least in part to the image acquisition component;
    a tray having a generally planar tray floor, substantially nonobstructive to light of at least one wavelength emitted by the first light source, and having a perimeter sidewall, wherein the sidewall substantially adjoins the tray floor and establishes a physical boundary for the tray floor that is open at least in part, wherein the sidewall rises above the tray floor to a specifiable extent;
    a bracket whereby the tray is removably attachable to the counter;
    a first hinge mechanism that links the tray to the bracket, wherein the tray is configured to rotate over a range that includes a first tray floor orientation that is substantially horizontal when the counter is in its normal operating orientation, and that further includes a second tray floor orientation that is tilted sufficiently to direct units resting on the tray floor toward the sidewall open part;
    a pivotable stop bar affixed to the bracket by a second hinge mechanism, wherein tray tilt coupled to the stop bar opens a gap between the stop bar and the tray sidewall open part; and
    a collection chute positioned beneath the sidewall open part, whereby units directed toward the sidewall open part and spilled therefrom are gathered into a lower opening of the collection chute.

2. The machine-vision-based counter of claim 1, wherein the image acquisition component further comprises:
    a machine vision transducer, whereby data correlated to the relative intensity of radiation impinging on an imaging plane of the machine vision transducer in at least one frequency range is converted to a form suitable for transmission and processing;
    a mount configured to affix the transducer with respect to the background field; and
    a transducer data management function, whereby machine vision output data corresponding to the background field and any units present thereupon is transmitted to the image processor.

3. The machine-vision-based counter of claim 2, wherein the image acquisition component further comprises:
    a filter interposed between the machine vision transducer and substantially all light impinging thereupon, whereby light having a spectral component of interest is passed relatively free of impediment to the transducer, and light lacking a spectral component of interest is substantially blocked from the transducer;
    a focusing element, whereby a pattern of light from the background field, directed in part toward the image acquisition component, is formed into an image at least at the imaging plane of the machine vision transducer; and
    an image converter for transforming an image at the imaging plane of the machine vision transducer into an array of pixels, wherein each pixel has a value representing an intensity of light falling thereupon.

4. The machine-vision-based counter of claim 1, further comprising:
    a communication interface component, wherein the communication interface component provides information interchange in at least one direction between the counter and a device external to the counter.

5. The machine-vision-based counter of claim 1, wherein the first light source further comprises:
    a first emitter configured to emit light in the form of a sequence of intervals of relatively high brightness light emission interspersed with intervals of relatively low brightness light emission; and
    a synchronizing control signal generator whereby the first light source emission sequence is coordinated with operation of the image acquisition component.

6. The machine-vision-based counter of claim 1, wherein the first light source further comprises a first emitter configured to apply light sequentially over an array of discrete locations cumulatively comprising the background field, wherein light directed to the image acquisition component from the locations in succession permits acquisition of an image of the background field and any imageable units located thereon.

7. The machine-vision-based counter of claim 1, wherein the first light source further comprises:
  a substantially uniformly emissive panel positioned distal to the image acquisition component, whereby subject units positioned between the background field and the machine vision transducer are illuminated in silhouette;
  a substantially diffusely emissive panel, positioned distal to the background field and any subject units, so illuminating the background field and any subject units that light reflected therefrom is applied to the image acquisition component; or
  at least one source of light substantially comprising a discrete point source, positioned distal to the background field and any subject units, so illuminating the background field and any subject units that light reflected therefrom is applied to the image acquisition component.

8. The machine-vision-based counter of claim 1, further comprising a second light source, wherein the second light source is configured to emit light that includes at least an emitted color spectrum component not used in image processing associated with the first light source, wherein the second light source is so located that at least one attribute of the units is differently detected by the image acquisition component using light from the first light source and light from the second light source.

9. The machine-vision-based counter of claim 1, wherein the image processor is configured with:
  a data interface function, wherein a data stream from the image acquisition component is interpreted as an image in the form of an array of pixels representing the brightness of a plurality of locations on the background field, including any countable units located thereon;
  a localization function, wherein at least one region within image limits of the background field is identified as a region to analyze for countable units;
  a pattern recognition function, wherein successive subregions within a region to analyze are compared to a unit model in search of a match;
  a pattern match criterion, wherein a sufficiently small difference between the unit model and a subregion is interpreted as a match;
  a unit count function, wherein identification of a match increments the count;
  an erasure function, wherein incrementation of the unit count function marks as blank such pixels in the region to analyze as are associated with the match;
  a completion function, wherein an identified region to analyze, lacking subregions satisfying the pattern match criterion, is reidentified as empty; and
  a count control function, wherein the count control function determines a unit count function sequential repetition rate.

10. The machine-vision-based counter of claim 1, further comprising
  a unit geometric pattern database, wherein the database includes recordation for a specified type of unit, wherein the unit recordation comprises a combination of size, shape, and at least one spatial orientation for the type of unit, whereby an image of a unit acquired by the image acquisition component is identifiably associable with the corresponding unit recordation.

11. The machine-vision-based counter of claim 1, further comprising:
  an actively-transmitting scanner, further comprising:
    a moving light beam, narrowly illuminating at least a single linear segment of area within a specified radius of the counter;
    a detector for reflected light originating in the moving light beam, wherein the detector converts the reflected light to a data bit sequence containing at least one recognizable code, wherein the code comprises a counter-related datum; and
  an electronic output signal to transfer the code to the counter controller;
    a data correlation function, wherein the transferred code and a reference code are compared; and
    a control function positively enabling at least one counter operation only if the correlation function result meets a specified criterion.

* * * * *

UNITED STATES PATENT AND TRADEMARK OFFICE
CERTIFICATE OF CORRECTION

| | | |
|---|---|---|
| PATENT NO. | : 7,599,516 B2 | Page 1 of 1 |
| APPLICATION NO. | : 11/331343 | |
| DATED | : October 6, 2009 | |
| INVENTOR(S) | : Limer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 937 days.

Signed and Sealed this

Twenty-eighth Day of September, 2010

David J. Kappos
*Director of the United States Patent and Trademark Office*